United States Patent [19]
Sabb et al.

[11] Patent Number: 5,468,875
[45] Date of Patent: Nov. 21, 1995

[54] 1-AZABICYCLOHEPTANE DERIVATIVES

[75] Inventors: Annmarie L. Sabb, Pennington; Reinhardt P. Stein, Monmouth Junction, both of N.J.

[73] Assignee: American Home Products Corporation, Madison, N.J.

[21] Appl. No.: 362,695

[22] Filed: Dec. 22, 1994

[51] Int. Cl.⁶ .................................................. C07D 209/02
[52] U.S. Cl. ........................................ 548/512; 546/112
[58] Field of Search ............................ 548/512; 546/112

[56] References Cited

U.S. PATENT DOCUMENTS

| | | | |
|---|---|---|---|
| 3,843,660 | 10/1974 | Dygos | 260/293.54 |
| 3,932,429 | 1/1976 | Takeda et al. | 260/295.5 B |
| 4,118,393 | 10/1978 | Fanshawe et al. | 260/326.5 B |
| 4,222,936 | 9/1980 | Mason et al. | 260/326.62 |
| 4,612,319 | 9/1986 | King | 514/305 |
| 4,697,019 | 9/1987 | King | 546/112 |
| 4,870,081 | 9/1989 | Orlek et al. | 546/112 |
| 4,937,239 | 6/1990 | Lauffer et al. | 514/183 |
| 4,996,201 | 2/1991 | Bergmeier et al. | 514/212 |

FOREIGN PATENT DOCUMENTS

| | | | |
|---|---|---|---|
| 0257741 | 3/1988 | European Pat. Off. | 514/183 |
| 0039697 | 9/1975 | Japan | 548/512 |

OTHER PUBLICATIONS

CA 117:26271y Absolute . . . heptanes. Boelsterli et al., p. 684, 1992.
K. Fukuda et al., TiPS, 4–10, Dec. 1989, Supplement, Selective . . . subtypes.
T. I. Bonner, TiPS 11–15, Dec. 1989 Supplement, New . . . receptors.
T. T. Soncrant et al., Psychopharmacology 112:421–427 (1993), Memory . . . disease.
M. Williams, Curr. Opin. Invest. Drugs 2(5):541–544 (May 1993), Tacrine . . . approval.
R. T. Bartus et al., Science 217:408–417 (Jul. 1982), The Cholinergic . . . Dysfunction.
CA 86:177317k Pharmaceutical . . . compounds. Bauman p. 379, 1977.
CA87:133868g Quaternary . . . compounds. Bauman, p. 630, 1977.

*Primary Examiner*—Joseph K. McKane
*Attorney, Agent, or Firm*—Richard K. Jackson

[57] ABSTRACT

The compound of the formula:

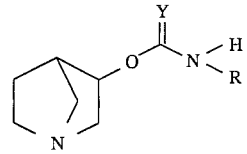

where R is H, alkyl, haloalkyl, cycloalkyl, alkenyl or alkynyl; Y is oxygen, sulfur or $NR_2$ where $R_2$ is H or alkyl; or a pharmaceutically acceptable salt thereof, are centrally active muscarinic agents.

18 Claims, No Drawings

1-AZABICYCLOHEPTANE DERIVATIVES

BACKGROUND OF THE INVENTION

Cognitive disorders have many components including forgetfulness, confusion, memory loss, attentional deficits, and deficits in visual perception. Some of the symptoms of cognitive disorders are associated with decreased levels of the neurotransmitter, acetylcholine. Neurological illnesses related to cholinergic deficiency include presenile dementia and senile dementia of the Alzheimer's type (SDAT), Parkinson's disease, Downe's Syndrome, and dementia pugilistica.

The "cholinergic hypothesis" [R. T. Bartus, et al., Science, 217, 408–417 (Jul. 30, 1982)] suggests that memory loss due to decreased levels of acetylcholine can be ameliorated by correcting the levels of acetylcholine in the brain using an acetylcholine releasing agent, an acetylcholine esterase inhibitor, or by using a drug which mimics acetylcholine (cholinomimetic). Marketing of the acetylcholine esterase inhibitor, tactine, has demonstrated that improvement in memory can be shown in patients with mild to moderate Alzheimer's Disease [M. Williams, Curr. Opin. Invest. Drugs, 2(5), 541–544 (May 1993) ]. The utility of this drug is limited, however, because of adverse side effects especially at the higher doses where it is most effective. Clinical studies using the natural alkaloid, arecoline, a cholinergic agonist, have also demonstrated memory improvement in patients with mild to moderate Alzheimer's Disease. Because of the short half-life of arecoline, the clinical study was done using continuous infusion of the drug over a 2 week period. In addition, a peripheral muscarinic antagonist, N-methylscopolamine, was also administered during the study to prevent potential autonomic side effects. [T. T. Soncrant et al., Psychopharmacology, 112, 421–427 (1993)].

Cholinergic receptors which bind to and are activated by the alkaloid, muscarine, are called muscarinic receptors. Three pharmacologically defined subtypes of muscarinic receptors have been identified. They are referred to as M1, M2, and M3 based upon their affinity for the M1 antagonist, pirenzepine, the M2 antagonist, AFDX- 116, and the M3 antagonist, 4-[(diphenylacetyl)oxy]-1,1-dimethylpiperidinium iodide (4-DAMP). Five different human muscarinic receptors have been cloned. The Hm1 (human m1) receptor is found primarily in the frontal cortex. [T. I. Bonner, Trends in Pharmacological Sciences, supplement, July 20–27 (1989) p11–15,]. Activation of the m1 receptor results in an increase in phosphoinositol hydrolysis (PI turnover).[K. Fukuda, et al. , Ibid,. p. 4–10]. Carbachol, like muscarine, is able to fully activate m1 receptors. These two compounds, however, contain a quaternary ammonium group and as a result are not able to enter the CNS.

U.S. Pat. No. 4,996,201 discloses a group of centrally active muscarinic agents useful as analgesic agents, sleep aids, treating the symptoms of senile dementia. Compound (II) is disclosed as an example of an analogue of oxotremorine.

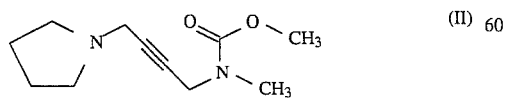
(II)

U.S. Pat. No. 4,937,239 discloses some oximinocarbamates as having muscarinic activity.

European Patent Application 0 257 741 discloses exo-1-azabicyclo[ 3.3.1]non-3-yl-N-methylcarbamate in Example 11, exo-1-azabicyclo[ 3.2.1oct-6-yl-N-methylcarbamate in Example 20 and exo-1-azabicyclo[ 3.3.1]non-3-yl-N,N-dimethylcarbamate in Example 24 as having muscarinic activity.

DESCRIPTION OF THE INVENTION

This invention provides azabicyclic compounds which are able to pass into the CNS and bind to and stimulate central $M_1$ muscarinic acetylcholine receptors and are useful agents for treating symptoms of cholinergic insufficiency involving cognitive disorders, specifically the impaired memory associated with a decrease in the neurotransmitter, acetylcholine. The compounds of the present invention are characterized by the general formula

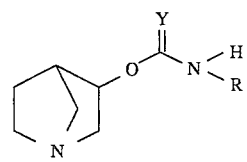

where

R is H, alkyl of 1 to 6 carbon atoms, haloalkyl or 1 to 6 carbon atoms, cycloalkyl of 3 to 6 carbon atoms, alkenyl of two to 6 carbon atoms or alkynyl of 2 to 6 carbon atoms;

Y is oxygen, sulfur or $NR_2$ where $R_2$ is H or alkyl of 1 to 6 carbon atoms;

or a pharmaceutically acceptable salt thereof. These compounds exist as endo or exo racemates or enantiomers and are prepared by the general synthetic methods detailed in Scheme I and Scheme II. The stereo and optical isomers may be isolated by conventional means or they may be prepared directly by stereospecific synthetic methods.

SCHEME I

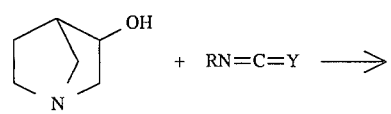

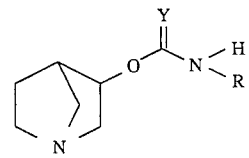

SCHEME II

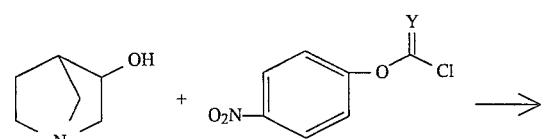

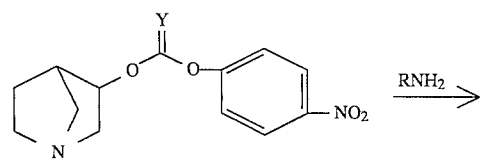

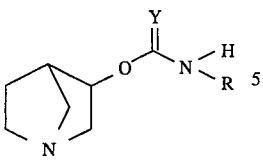

where R and Y are defined above.

Referring to Scheme I, the requisite 1-azabicyclo[2.2.1]heptan-3-ol is allowed to react with an appropriate isocyanate or isothiocyanate in an organic solvent, such as tetrahydrofuran (THF) in the presence of a base, such as pyridine at elevated temperatures to give products of the present invention. Or referring to Scheme II, the requisite 1-azabicyclo[2.2.1]heptan-3-ol is allowed to react with 4-nitrobenzoyl chloride, and the product of that reaction is allowed to react with the desired amine in an organic solvent, such as dichloromethane, in the presence of a base, such as pyridine, at ambient temperature to give products of this invention. The free base is converted to a desirable pharmaceutically acceptable salt by reaction with the respective acid. Among applicable pharmaceutically acceptable acids from which the salts may be made, there may be mentioned acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids.

It has been discovered that stereochemistry is critically important for functional m1 muscarinic agonism. For example, it has been found that the methylene bridged compounds of this invention possess enhanced muscarinic agonism in the exo azacycloheptane analog, Example 1, but not the endo azacycloheptane analog.

In addition, the thiocarbonyl analogs have greater affinity for the m1 receptor than their corresponding carbonyl analogs and both enantiomers are m1 agonists.

The preferred compounds of the present invention are those in which R is alkyl of 1 to 3 carbon atoms, cycloalkyl of 3 to 4 carbon atoms and alkynyl of 2 to 3 carbon atoms, of exo configuration, most preferably the levo isomer, and the thionyl carbamates in exo configuration, both levo and dextro isomers.

The following examples are presented for illustrative purposes only and are not to be construed as limitations for the disclosed invention. Those skilled in the art will be aware of other methods of preparing compounds of this invention. The starting materials or intermediates are available commercially or can be prepared by standard literature procedures.

EXAMPLE 1

(exo)-Methylcarbamic acid 1-aza-bicyclo[2.2.1]hept-3-yl ester

A solution of 452 mg (4 mmole) of (exo-)-1-azabicyclo[2.2.1]heptan-3-ol in 15.0 mL dry THF and 3.5 mL dry pyridine was treated with methyl isocyanate (800 mg, 14 mmole, 0.8 mL) and stirred at 50°–60° C. under nitrogen 24 hours and then at room temperature for 2 days. Removal of solvent at reduced pressure and flash chromatography through alumina using methanol (2–10%) in ethyl acetate yielded 430 mg (63%) of title compound as a waxy white solid, mp: 85–95 C. A second purification on alumina using ethanol (1–6%) in ethyl acetate gave 162 mg of a waxy solid, mp: 92°–96° C. MS (EI, m/z): 170 ($M^+$) plus 71 (CH3NCO, $M^+$).

Elemental analysis for $C_8H_{14}N_2O_2$ 0.33 CH$_3$NCO Calc'd: C, 55.02; H, 8.00; N, 17.26 Found: C, 55.00; H, 8.19; N, 17.21

EXAMPLE 2

(+)-(exo)-Methylcarbamic acid 1-aza-bicyclo[2.2.1]hept-3-yl ester

Following the procedure of Example 1, (+)-(exo-(−)-1-azabicyclo[2.2.1]-heptan- 3-ol was allowed to react with methyl isocyanate in dry THF and pyridine, to give the title compound, mp: 88–93 C.; O.R.: [alpha]25/D=+17.28 (methanol).

Elemental analysis for $C_8H_{14}N_2O_2$ Calc'd: C, 56.45; H, 8.29; N, 16.46 Found: C, 56.15; H, 8.45; N, 16.59

EXAMPLE 3

(−)-(exo)-Methylcarbamic acid 1-aza-bicyclo[2.2.1]hept-3-yl ester

A solution of (−)-(exo)-1-azabicyclo[2.2.1]heptane-3-ol (1.20 g, 10.6 mmole) in dry THF (20 mL) and dry pyridine (4 mL) was treated with excess methyl isocyanate (periodic additions) and stirred at 60° C. (oil bath temperature) in a nitrogen atmosphere for 6 hours. Removal of solvent at reduced pressure and flash chromatography through alumina using methanol (1.5–4%) in ethyl acetate yielded 0.99 g (5.8 mmole, 55%) title compound as a white solid: m.p. 97°–98° C. IR (KBr): 0, 2990, 1720, 1630, 1280, 1150, 1040, 970, 840, 760 cm$^{-1}$. NMR (DMSO): d= 0.97 (1H, mult); 1.49 (1H, m); 2.15 (1H, d [J=8.6 Hz]); 2.24 (1H, m); 2.42 (1H, d [J=4.8 Hz]); 2.52 (3H, d[J=4.6 Hz], NMe); 2.74 (1H, m); 4.22 (1H); 6.93 (1H). MS (CI, m/z): 171 $(M+H)^{.+}$, 112. O.R.: [alpha]25/D=−17.40 (methanol).

Elemental analysis for $C_8H_{14}N_2O_2$ Calc'd: C, 56.45; H, 8.29; N, 16.46 Found: C, 56.22; H, 8.30; N, 16.46

EXAMPLE 4

(exo)-Methylthiocarbamic acid 1-aza-bicyclo[2.2.1]hept-3-yl ester

A solution of (exo)-1-azabicyclo[2.2.1]heptane-3-ol (1.0 g, 8.9 mmoL) in dry THF (20 mL) and dry pyridine (4 mL) was treated with excess methyl isothiocyanate (periodic additions) while heating (oil bath temperature 90° C.) in a nitrogen atmosphere. The reaction was followed by TLC (silica gel, 10% methanol in methylene chloride). After 18 hours, methanol was added to destroy excess methyl isothiocyanate and the volatiles were removed under vacuum. The dark residue was purified by flash column chromatography on alumina eluting with a gradient of 0.5–5% methanol in ethyl acetate. A second purification using a short column of silica gel and 5–7% methanol in methylene chloride gave the title compound (240 mg, 15%): mp: 138–141 C.; MS (EI, m/z): 186($M^+$).

Elemental analysis for $C_8H_{14}N_2OS$. 0.125 H$_2$O Calc'd: C, 50.97; H, 7.62; N, 14.86 Found: C, 50.80; H, 7.32; N, 14.70

EXAMPLE 5

(+)-(exo)-Methylthiocarbamic acid 1-aza-bicyclo[2.2.1]hept-3-yl ester

The racemic mixture prepared in Example 4 was resolved by HPLC to give the title compound, mp: 175–176 C.; O.R. [alpha] 25/D: +27.82 (methanol); MS (EI, m/z): 186(M$^+$).

Elemental analysis for $C_8H_{14}N_2OS$ Calc'd: C, 51.58; H, 7.58; N, 15.04 Found: C, 51.73; H, 7.72; N, 14.84

EXAMPLE 6

(−)-(exo)-Methylthiocarbamic acid 1-aza-bicyclo[2.2.1]hept-3-yl ester

The racemic mixture prepared in Example 4 and resolved by HPLC gave the title compound, mp: 167–170 C.; O.R. [alpha] 25/D: −30.21 (methanol); MS (EI, m/z): 186(M$^+$).

Elemental analysis for $C_8H_{14}N_2OS.0.1 H_2O$ Calc'd: C, 51.09; H, 7.61; N, 14.89 Found: C, 51.08; H, 7.48; N, 14.93

EXAMPLE 7

(+)-(exo)-Ethylcarbamic acid 1-aza-bicyclo[2.2.1]hept-3-yl ester

Following the procedure of Example 1, (+)-(exo-)-1-azabicyclo[2.2.1]-heptan- 3-ol was allowed to react with ethyl isocyanate in dry THF and pyridine, to give the title compound, m.p.: 115–117 C.; O.R. [alpha]25/D=+17.12 (MeOH).

Elemental analysis for $C_9H_{16}N_2O_2$ Calc'd: C, 58.67; H, 8.75; N, 15.21 Found: C, 58.53; H, 8.87; N, 15.34

EXAMPLE 8

(−)-(exo)-Ethylcarbamic acid 1-aza-bicyclo[2.2.1]hept-3-yl ester

Following the procedure of Example 1, (−)-(exo-)-1-azabicyclo[2.2.1 ]-heptan- 3-ol was allowed to react with ethyl isocyanate in dry THF and pyridine, to give the title compound, m.p. 110–114 C.; O.R. [alpha] 25/D= −15.38 (MeOH).

Elemental analysis for $C_9H_{16}N_2O_2$. 0.1 $H_2O$ Calc'd: C, 58.11; H, 8.78; N, 15.06 Found: C, 58.02; H, 8.78; N, 15.19

EXAMPLE 9

(exo)-(2.2.2-Trifluoroethyl)carbamic acid 1-aza-bicyclo[2.2.1]hept-3-yl ester (exo)-1-Azabicyclo[2.2.1]heptan-3-ol (250 mg, 22.1 mmoL) in methylene chloride dried over magnesium sulfate (35 mL) was cooled to 10° C. p-Nitrophenylchloroformate (450 mg, 22.3 mmol) and dry pyridine (1 mL) were added and the reaction mixture was stirred for 1.5 hours under a nitrogen atmosphere. 2,2,2-Trifluoroethylamine (0.24 mL, 3 mmoL) was added and the reaction mixture was allowed to stir at room temperature for 3 days. The volatiles were removed under vacuum and the residue was purified by flash column chromatography on silica gel eluting with 2–3% methanol in methylene chloride containing one-quarter percent ammonium hydroxide to obtain the product as a white solid: (50 mg, 10%) m.p. 123– 125 C.

Elemental analysis for $C_9H_{13}F_3N_2O_2.0.4 H_2O$ Calc'd: C, 44.05; H, 8.67; N, 11.41 Found: C, 43.77; H, 5.30; N, 11.42

EXAMPLE 10

(−)-(exo)-(2.2.2-Trifluoroethyl)carbamic acid 1-aza-bicyclo[2.2.1]hept-3-yl ester Following the procedure of Example 9, (−)-(-exo-)-1-azabicyclo[2.2.1]heptan -3-ol was allowed to react with 4-nitrophenylchloroformate and the intermediate was treated with 2,2,2-trifluoroethylamine to give the title compound, mp 137–138 C. O.R. alpha] 25/D=−12.38 (methanol).

Elemental analysis for $C_9H_{13}F_3N_2O_2$. 0.05 $H_2O$ Calc'd: C, 44.83; H, 5.45; N, 11.55 Found: C, 45.06; H, 5.44; N, 11.28

Employing (+)-(exo-)-1-azabicyclo[2.2.1]-heptan-3-ol as the initial reactant in this example provides the corresponding dextro isomer (+)-(exo-)-(2,2,2-trifluoroethyl)carbamic acid 1-aza-bicyclo[2.2.1]hept-3-yl ester.

EXAMPLE 11

(exo)-Cyclopropylcarbamic acid 1-aza-bicyclo[2.2.1]hept-3-yl ester

Following the procedure of Example 9, (exo-)-1-azabicyclo[2.2.1]heptan-3-ol was allowed to react with 4-nitrophenylchloroformate and the intermediate was treated with cyclopropylamine to give the title compound, m.p. 108–114C.

Elemental analysis for $C_{10}H_{16}N_2O_2$. 0.15 $H_2O$ Calc'd: C, 60.37; H, 8.26; N, 14.05 Found: C, 60.39; H, 8.11; N, 13.72

EXAMPLE 12

(−)-(exo)-Cyclopropylcarbamic acid 1-aza-bicyclor2.2.1]hept-3-yl ester

Following the procedure of Example 9, (−)-(exo-)-1-azabicyclo[2.2.1]-heptan- 3-ol was allowed to react with 4-nitrophenylchloroformate and the intermediate was treated with cyclopropylamine to give the title compound as an amorphous solid. O.R. alpha] 25/D=−14.96 (methanol).

Elemental analysis for $C_{10}H_{16}N_2O_2$. 0.33 $H_2O$ Calc'd: C, 59.39; H, 8.31; N, 13.85 Found: C, 59.12; H, 8.18; N, 14.07

Employing (+)-(exo-)-1-azabicyclo[2.2.1]-heptan-3-ol as the initial reactant in this example provides the corresponding dextro isomer (+)-(exo-)-cyclopropylcarbamic acid acid 1-aza-bicyclo[2.2.1]hept-3-yl ester.

EXAMPLE 13

(−)-(exo)-Propargylcarbamic acid 1-aza-bicyclo[2.2.1]hept-3-yl ester

Following the procedure of Example 9, (−)-(exo-)-1-azabicyclo[2.2.1]-heptan- 3-ol was allowed to react with 4-nitrophenylchloroformate and the intermediate was treated with propargylamine to give the title compound, m.p. 114–117 C.; O.R. alpha] 25/D=−16.10 (methanol).

Elemental analysis for $C_{10}H_{14}N_2O_2$. 0.25 $H_2O$ Calc'd: C, 60.44; H, 7.35; N, 14.10 Found: C, 60.31; H, 7.15; N, 13.86

Employing (+)-(exo-)-1-azabicyclo[2.2.1]-heptan-3-ol as the initial reactant in this example provides the corresponding dextro isomer (+)-(exo-)-propargylcarbamic acid 1-aza-bicyclo[2.2.1]hept-3-yl ester.

The affinity of the compounds of this invention for muscarinic receptors was established by testing them in accordance with the standard pharmacomogical test procedures in which the compound's ability to compete with [$^3$H]QNB binding and by analysis of PI hydrolysis stimulation in accordance with the following test procedures:

percentage of the mean value obtained for carbachol (EC$_{50}$= 8.0 μM).

The results of these studies are given below:

| Compound # | ml $^3$H QNB Binding in CHO cells Ki (μM) | % PI Hydrolysis ml receptors in CHO cells 30x Ki (μM) carb=100% | % PIHydrolysis ml receptors in CHO cells maximum % cabachol=100% | % PI Hydrolysis ml receptors in CHO cells ED$_{50}$ |
|---|---|---|---|---|
| IN VITRO PHARMACOLOGY | | | | |
| Example 1 | 29.3 | 61.9 | 54.9 | 6.9 |
| Example 2 | 41.8 | | | |
| Example 3 | 26.61 | 71.9 | 68.7 | 9.8 |
| Example 4 | 3.72 | 21.8 | | |
| Example 5 | 6.93 | 48.6 | 51.5 | 2.9 |
| Example 6 | 14.55 | 69.7 | 69.7 | 6.3 |
| Example 7 | 14.31 | | | |
| Example 8 | 21.49 | 58.8 | | |
| Example 9 | 14.48 | | | |
| Example 10 | 17.58 | | | |
| Example 11 | 1.81 | 10.1 | | |
| Example 12 | 20.51 | | | |
| Example 13 | 14.55 | 39.4 | | |
| Arecoline | 4.8 | | 70 | 11.0 |

The binding affinity of the compounds of this invention at muscarinic receptor subtypes was determined by incubating triplicate samples of homogenized Chinese Hamster Ovary (CHO) cells which had been transfected with CMV vector containing cDNA expressing individual muscarinic receptor subtypes, for one hour at 37° C. with 0.23 nM radiolabeled quinuclidinyl benzilate [$^3$H]QNB, a representative compound of this invention, and a volume of 10 mM phosphate buffer to obtain a final incubation volume of 1000 μL. Vehicle and 2 μM atropine sulfate are substituted for the test solution to determine total and non-specific bindings, respectively. After incubation, the solutions are filtered and the filter paper is subjected to scintillation spectroscopy for radioactivity counting. Specific binding in the presence of the compound of this invention is expressed as a percentage of the atropine-sensitive binding. A concentration-response evaluation is obtained through non-linear regression analysis to obtain an IC$_{50}$ and/or K$_i$ value. This procedure is based on that of Tonnaer et al, Life Sci., 40, 1981 (1987).

The ability of the compounds of this invention to stimulate hydrolysis of phosphoinositide (PI) in chinese Hamster Ovary (CHO) cells which had been transfected with CMV vector containing cDNA expressing M$_1$ acetylcholine receptors was determined in accordance with the procedure of El-Fakahany et al, J. Pharmacol. Exp. Ther. 257,938 (1991), whereby PI hydrolysis is performed in reaction tubes, each containing 880 μL Kreb's Buffer, 10 μL of 1.0 M LiCl solution, 10 μL of the compound representative of this invention or control vehicle, and 100 μL of CHO cell suspension in Kreb's Buffer (1,000,000 cells per mL). The tubes are incubated for one hour at 37° C. The reaction is quenched with chloroform and the phosphatidyl inositols are extracted with methanol and chloroform. Phase separation is assured with the addition of methanol and water followed by centrifugation. The tritiated inositol phosphates are recovered on BioRad AG 1-X8 anion exchange resin in the formate cycle. After washing the resin with water and myo-inositol, the inositol phosphates are eluted with ammonium formate/formic acid, collected and subjected to liquid scintillation spectroscopy. The results are expressed as a

IN VIVO PHARMACOLOGY

The compound of Example 3, representative of the other compounds of this invention, was also tested in accordance with the procedure of Symons et al, Soc. Neuroscience Abstracts 12:2, 897 (1986) in which Male CFW mice, 25 to 35 grams in weight are given the test compound in suitable vehicle plus 0.3 mg/kg scopolamine.HBr in suitable vehicle, i.p.(3 groups of 12 animals each) or vehicle alone (1 group of 12 animals ) or vehicle plus scopolamine.HBr (1 group of 12 animals). The mice are placed in a swim tank, individually, containing 10 cm H$_2$O for a period of 5 minutes and the distance each animal swims is recorded. The mean swimming distance for the group is compared with controls and the test compound is considered active at a dose that significantly reduces the distance swam from the scopolamine control mean swim distance. Similarly the test compound is considered active if its results do not differ from the vehicle control mean. The compound of Example 3, representative of the other compounds of this invention, exhibited activity by reversing the hyperactivity of scopolamine treated animals in this standard experimental test procedure at a minimum effective dose of MED=30 mg/kg.

The compound of Example 3 was also tested in the eight arm radial maze test procedure in which Sprague-Dawley male rats at 85% of their free feeding weight are trained to obtain two food pellets from food cups placed at the ends of four of the eight arms radiating from a circular central area of the maze, in a five minute period. After training to a level of error (rerum to a previously entered arm is error) equal to or less than 2, the rats performance is disrupted with scopolamine HBr (0.3 mg/kg, s.c.) and test compound dosage (i.p.). The number of errors are then determined and compared with control receiving scopolamine alone. The compound of Example 2 exhibited a reversal of scopolamine disrupted rat performance at a minimum effective dose of MED=1 mg/kg.

Hence, the compounds of this invention demonstrated high affinity for muscarinic receptors (especially the m 1 receptor) and are therefore useful in the treatment of disease states associated with insufficient cerebral acetylcholine production or release.

Based upon this receptor binding information and PI hydrolysis, the compounds of this invention are characterized as useful in the treatment of cognitive disorders associated with decreased levels of cerebral acetylcholine production or release, such as presenile dementia, senile dementia of the Alzheimer's type, Parkinson's disease, Downe's Syndrome and dementia pugilitica.

As such, the compounds may be administered neat or with a pharmaceutical carder to a patient in need thereof. The pharmaceutical carder may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carder is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carder such as water, an organic solvent, a mixture of both or pharmaceutically acceptable oils or fat. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carder can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from cerebral acetylcholine insufficiency must be subjectively determined by the attending physician. The variables involved include the severity of the dysfunction, and the size, age and response pattern of the patient.

What is claimed is:
1. A compound of the formula:

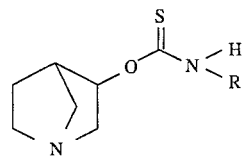

where
R is H, alkyl of 1 to 6 carbon atoms, haloalkyl or 1 to 6 carbon atoms, cycloalkyl of 3 to 6 carbon atoms, alkenyl of two to 6 carbon atoms or alkynyl of 2 to 6 carbon atoms;
or a pharmaceutically acceptable salt thereof.

2. A compound of claim 1 in which R is alkyl of 1 to 3 carbon atoms, cyclo-alkyl of 3 to 4 carbon atoms or alkynyl of 2 to 3 carbon atoms, of exo configuration.

3. A compound selected from the group consisting of:
(exo)-methylcarbamic acid 1-aza-bicyclo[2.2.1]hept-3-yl ester, or a pharmaceutically acceptable salt thereof;
(−)-(exo)-methylcarbamic acid 1-aza-bicyclo[2.2.1]hept-3-yl ester, or a pharmaceutically acceptable salt thereof;
(exo)-methylthiocarbamic acid 1 aza-bicyclo[2.2.1]hept-3-yl ester, or a pharmaceutically acceptable salt thereof;
(+)-(exo)-methylthiocarbamic acid 1-azabicyclo[2.2.1]hept-3-yl ester, or a pharmaceutically acceptable salt thereof;
(−)-(exo)-methylthiocarbamic acid 1-azabicyclo[2.2.1]hept-3-yl ester, or a pharmaceutically acceptable salt thereof;
(+)-(exo)-ethylcarbamic acid 1-azabicyclo[2.2.1]hept-3-yl ester, or a pharmaceutically acceptable salt thereof;
(−)-(exo)-ethylcarbamic acid 1-azabicyclo[2.2.1]hept-3-yl ester or a pharmaceutically acceptable salt thereof;
(exo)-(2,2,2-trifluoro)ethylcarbamic acid 1 azabicyclo[2.2.1]heptyl-3-yl ester, or a pharmaceutically acceptable salt thereof;
(−)-(exo)-(2,2,2-trifluoro)ethylcarbamic acid 1 azabicyclo[2.2.1]heptyl-3-yl ester, or a pharmaceutically acceptable salt thereof;
(+)-(exo)-(2,2,2-trifluoro)ethylcarbamic acid 1 azabicyclo[2.2.1]heptyl-3-yl ester, or a pharmaceutically acceptable salt thereof;
(exo)-cyclopropylcarbamic acid 1-azabicyclo[2.2.1]hept-3-yl ester or a pharmaceutically acceptable salt thereof;
(−)-(exo)-cyclopropylcarbamic acid 1-azabicyclo[2.2.1]hept-3-yl ester, or a pharmaceutically acceptable salt thereof;
(+)-(exo)-cyclopropylcarbamic acid 1-azabicyclo[2.2.1]hept-3-yl ester, or a pharmaceutically acceptable salt thereof;
(−)-(exo)-propargylcarbamic acid 1- azabicyclo[2.2.1]hept-3-yl ester, or a pharmaceutically acceptable salt thereof; and
(+)-(exo)-propargylcarbamic acid 1- azabicyclo[2.2.1]hept-3-yl ester, or a pharmaceutically acceptable salt thereof.

4. The compound of claim 3 which is (exo)-methylcarbamic acid 1-azabicyclo[ 2.2.1]hept-3-yl ester, or a pharmaceutically acceptable salt thereof.

5. The compound of claim 3 which is (−)-(exo)-methylcarbamic acid 1-azabicyclo[ 2.2.1]hept-3-yl ester, or a pharmaceutically acceptable salt thereof.

6. The compound of claim 3 which is (exo)-methylthiocarbamic acid 1-azabicyclo[2.2.1]hept-3-yl ester, or a pharmaceutically acceptable salt thereof.

7. The compound of claim 3 which is (+)-(exo)-methylthiocarbamic acid 1-azabicyclo[2.2.1]hept-3-yl ester, or a pharmaceutically acceptable salt thereof.

8. The compound of claim 3 which is (−)-(exo)-methylthiocarbamic acid 1-azabicyclo[2.2.1]hept-3-yl ester, or a pharmaceutically acceptable salt thereof.

9. The compound of claim 3 which is (+)-(exo)-ethylcarbamic acid 1-azabicyclo[2.2.1]hept-3-yl ester, or a pharmaceutically acceptable salt thereof.

10. The compound of claim 3 which is (−)-(exo)-ethylcarbamic acid 1-azabicyclo[2.2.1]hept-3-yl ester or a pharmaceutically acceptable salt thereof.

11. The compound of claim 3 which is (exo)-(2,2,2-trifluoro)ethylcarbamic acid 1 azabicyclo[2.2.1]heptyl-3-yl ester, or a pharmaceutically acceptable salt thereof.

12. The compound of claim 3 which is (−)-(exo)-(2,2,2-trifluoro)ethylcarbamic acid 1 azabicyclo[2.2.1]heptyl-3-yl ester, or a pharmaceutically acceptable salt thereof.

13. The compound of claim 3 which is (+)-(exo)-(2,2,2-trifluoro)ethylcarbamic acid 1 azabicyclo[2.2.1]heptyl-3-yl ester, or a pharmaceutically acceptable salt thereof.

14. The compound of claim 3 which is (exo)-cyclopropylcarbamic acid 1-azabicyclo[2.2.1]hept-3-yl ester or a pharmaceutically acceptable salt thereof.

15. The compound of claim 3 which is (−)-(exo)-cyclopropylcarbamic acid 1-azabicyclo[2.2.1]hept-3-yl ester, or a pharmaceutically acceptable salt thereof.

16. The compound of claim 3 which is (+)-(exo)-cyclopropylcarbamic acid 1-azabicyclo[2.2.1]hept-3-yl ester, or a pharmaceutically acceptable salt thereof.

17. The compound of claim 3 which is (−)-(exo)-propargylcarbamic acid 1-azabicyclo[2.2.1]hept-3-yl ester, or a pharmaceutic ally acceptable salt thereof.

18. The compound of claim 3 which is (+)-(exo)-propargylcarbamic acid 1-azabicyclo[2.2.1]hept-3-yl ester, or a pharmaceutically acceptable salt thereof.

* * * * *